United States Patent [19]
Toth et al.

[11] Patent Number: 5,837,839
[45] Date of Patent: Nov. 17, 1998

[54] DNA CODING SEQUENCES FOR MEVALONATE PYROPHOSPHATE DECARBOXYLASE

[75] Inventors: Matthew John Toth, Iselin; Leslie Robin Huwyler, West Orange, both of N.J.

[73] Assignee: Novartis Finance Corporation, New York, N.Y.

[21] Appl. No.: 733,825

[22] Filed: Oct. 18, 1996

Related U.S. Application Data

[60] Provisional application No. 60/005,652 Oct. 18, 1995.

[51] Int. Cl.$^6$ .......................... C12N 15/60; C12N 15/70; C12N 9/88; G01N 33/53
[52] U.S. Cl. .................. 536/23.2; 435/69.1; 435/232; 435/252.3; 435/320.1; 435/7.72
[58] Field of Search ............................ 435/232; 536/23.2

[56] References Cited

U.S. PATENT DOCUMENTS 4,652,639  3/1987  Stabinsky .................................. 536/27

FOREIGN PATENT DOCUMENTS 2241500A  9/1991  United Kingdom .

OTHER PUBLICATIONS

Fortkamp, E., et al., DNA, vol. 5, "Cloning and expression in Escherichia coli of a synthetic DNA for hirudin, the blood coagulation inhibitor in the leech", pp. 511–517, 1986.

Jabalquinto, A. M., et al., Archives of Biochemistry and Biophysics, vol. 225, "Evidence of essential arginyl residues in chicken liver mevalonate–5–pyrophosphate decarboxylase", pp. 338–343, 1983.

Castillo, M., et al., Neurochemistry International, vol. 18, "Inhibition of chick brain cholesterogenic enzymes by phenyl and phenolic derivatives of phenylalanine", pp. 171–174, 1991.

Zafra, M. F., et al., Neurochemical Research, vol. 12, "Effect of clofibrate on brain mevalonate–5–pyrophosphate decarboxylase", pp. 787–790, 1987.

Ashby, M. N., et al., The Journal of Biological Chemistry, vol. 267, "COQ2 is a candidate for the structural gene encoding para–hydroxybenzoate:polyprenyltransferase", pp. 4128–4136, 1992.

Sawamura, M., et al., The Journal of Biological Chemistry, vol. 267, "Liver mevalonate 5–pyrophosphate decarboxylase is responsible for reduced serum cholesterol in stroke–prone spontaneously hypertensive rat", pp. 6051–6055, 1992.

Shama Bhat, et al., Indian J. of Biochem. and Biophys., vol. 17, 1980, pp. 249–254,.

Dhe–Paganon, et al., Biochem. vol. 33, 1994, pp. 13355–13362.

Cardemil, et al., Meth. Enzymol., vol. 110, 1985, pp. 86–92.

Prous (1993) Drug New Perspectives 6:422–423.

Cuthbert and Lipsky (1995) Cancer Res. 55:1732–1740.

Cuthbert and Lipsky (1990) J. Biol. Chem 265:18568–18575.

Castillo et al (1991) Mol. Cell. Biol. 105:21–25.

Alvear et al (1982) 21:4646–4650 Biochemistry.

Chiew et al (1987) Biochem. Biophys. Acta 916:271–278.

*Primary Examiner*—Robert A. Wax
*Assistant Examiner*—William W. Moore
*Attorney, Agent, or Firm*—Gregory D. Ferraro

[57] ABSTRACT

We have cloned and expressed the cDNA for human liver mevalonate pyrophosphate decarboxylase, an enzyme of the cholesterol synthesis pathway. This cDNA encodes a 400 amino acid protein (43 kDa) which resembles the coding sequence of an unidentified and incomplete open reading frame adjacent to the COQ2 gene of *Saccharomyces cerevisiae*. We also found an expression sequence tag clone made from human infant brain cDNA to be almost identical to our cDNA sequence.

12 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1800 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 8..1207

( x i ) SEQUENCE DESCRIPTION: SEQ ID NO:1:

```
TGGGACC ATG GCC TCG GAG AAG CCG CTG GCG GCA GTC ACT TGT ACA GCG         49
        Met Ala Ser Glu Lys Pro Leu Ala Ala Val Thr Cys Thr Ala
         1               5                  10

CCG GTC AAC ATC GCG GTC ATC AAG TAC TGG GGC AAG CGC GAT GAA GAG         97
Pro Val Asn Ile Ala Val Ile Lys Tyr Trp Gly Lys Arg Asp Glu Glu
 15                  20                  25                  30

CTG GTT CTG CCC ATC AAC TCC TCC CTG AGC GTC ACT CTG CAC CAG GAC        145
Leu Val Leu Pro Ile Asn Ser Ser Leu Ser Val Thr Leu His Gln Asp
                 35                  40                  45

CAG TTA AAA ACC ACC ACA ACA GCC GTC ATC AGC AAG GAC TTC ACC GAG        193
Gln Leu Lys Thr Thr Thr Thr Ala Val Ile Ser Lys Asp Phe Thr Glu
             50                  55                  60

GAC CGG ATT TGG CTG AAT GGC CGG GAG GAG GAT GTG GGG CAG CCG AGG        241
Asp Arg Ile Trp Leu Asn Gly Arg Glu Glu Asp Val Gly Gln Pro Arg
         65                  70                  75

CTG CAG GCC TGC CTG CGG GAG ATC CGC TGC CTG GCC CGG AAG CGG AGG        289
Leu Gln Ala Cys Leu Arg Glu Ile Arg Cys Leu Ala Arg Lys Arg Arg
     80                  85                  90

AAC TCA CGG GAT GGG GAC CCG CTG CCC TCC AGC CTC AGC TGC AAG GTG        337
Asn Ser Arg Asp Gly Asp Pro Leu Pro Ser Ser Leu Ser Cys Lys Val
 95                 100                 105                 110

CAC GTG GCA TCG GTG AAC AAC TTC CCC ACG GCT GCG GGC CTG GCC TCC        385
His Val Ala Ser Val Asn Asn Phe Pro Thr Ala Ala Gly Leu Ala Ser
                115                 120                 125

TCA GCG GCG GGC TAT GCC TGC CTA GCC TAC ACC CTG GCC CGT GTC TAC        433
Ser Ala Ala Gly Tyr Ala Cys Leu Ala Tyr Thr Leu Ala Arg Val Tyr
            130                 135                 140

GGC GTG GAG AGT GAC CTC TCA GAA GTG GCT CGC CGG GGC TCA GGC AGC        481
Gly Val Glu Ser Asp Leu Ser Glu Val Ala Arg Arg Gly Ser Gly Ser
        145                 150                 155

GCC TGC CGG AGC CTG TAT GGG GGC TTT GTG GAG TGG CAG ATG GGA GAG        529
Ala Cys Arg Ser Leu Tyr Gly Gly Phe Val Glu Trp Gln Met Gly Glu
    160                 165                 170

CAG GCC GAC GGG AAG GAC AGC ATC GCT CGG CAA GTG GCC CCC GAG TCA        577
Gln Ala Asp Gly Lys Asp Ser Ile Ala Arg Gln Val Ala Pro Glu Ser
175                 180                 185                 190

CAC TGG CCT GAA CTC CGC GTG CTC ATC CTT GTG GTG AGC GCT GAG AAG        625
His Trp Pro Glu Leu Arg Val Leu Ile Leu Val Val Ser Ala Glu Lys
                195                 200                 205

AAG CTG ACA GGC AGT ACC GTG GGC ATG CGG GCC AGT GTG GAG ACC AGC        673
Lys Leu Thr Gly Ser Thr Val Gly Met Arg Ala Ser Val Glu Thr Ser
            210                 215                 220

CCC CTG CTT CGG TTC CGG GCC GAG TCC GTG GTG CCC GCG CGC ATG GCG        721
Pro Leu Leu Arg Phe Arg Ala Glu Ser Val Val Pro Ala Arg Met Ala
        225                 230                 235

GAG ATG GCC CGC TGC ATC CGG GAG CGA GAC TTC CCC AGC TTC GCC CAG        769
Glu Met Ala Arg Cys Ile Arg Glu Arg Asp Phe Pro Ser Phe Ala Gln
    240                 245                 250
```

```
CTG  ACC  ATG  AAG  GAC  AGC  AAC  CAG  TTC  CAC  GCC  ACC  TGC  CTC  GAC  ACC        817
Leu  Thr  Met  Lys  Asp  Ser  Asn  Gln  Phe  His  Ala  Thr  Cys  Leu  Asp  Thr
255                           260                      265                      270

TTC  CCG  CCC  ATC  TCT  TAC  CTC  AAT  GCC  ATC  TCC  TGG  CGC  ATC  ATC  CAC        865
Phe  Pro  Pro  Ile  Ser  Tyr  Leu  Asn  Ala  Ile  Ser  Trp  Arg  Ile  Ile  His
                    275                      280                      285

CTG  GTG  CAC  CGC  TTC  AAC  GCC  CAC  CAC  GGG  GAC  ACC  AAG  GTG  GCG  TAC        913
Leu  Val  His  Arg  Phe  Asn  Ala  His  His  Gly  Asp  Thr  Lys  Val  Ala  Tyr
               290                           295                      300

ACC  TTT  GAC  GCG  GGC  CCC  AAT  GCC  GTG  ATC  TTC  ACC  CTG  GAC  GAC  ACT        961
Thr  Phe  Asp  Ala  Gly  Pro  Asn  Ala  Val  Ile  Phe  Thr  Leu  Asp  Asp  Thr
          305                           310                      315

GTG  GCT  GAG  TTT  GTG  GCT  GCT  GTG  TGG  CAC  GGC  TTT  CCC  CCA  GGC  TCG       1009
Val  Ala  Glu  Phe  Val  Ala  Ala  Val  Trp  His  Gly  Phe  Pro  Pro  Gly  Ser
          320                      325                      330

AAT  GGA  GAC  ACG  TTT  CTG  AAG  GGG  CTG  CAG  GTG  AGG  CCG  GCC  CCT  CTC       1057
Asn  Gly  Asp  Thr  Phe  Leu  Lys  Gly  Leu  Gln  Val  Arg  Pro  Ala  Pro  Leu
335                      340                      345                      350

TCA  GCT  GAG  CTT  CAG  GCT  GCG  CTG  GCC  ATG  GAG  CCG  ACC  CCC  GGT  GGG       1105
Ser  Ala  Glu  Leu  Gln  Ala  Ala  Leu  Ala  Met  Glu  Pro  Thr  Pro  Gly  Gly
                    355                      360                      365

GTC  AAA  TAC  ATC  ATT  GTC  ACT  CAG  GTG  GGG  CCA  GGG  CCT  CAA  ATC  CTG       1153
Val  Lys  Tyr  Ile  Ile  Val  Thr  Gln  Val  Gly  Pro  Gly  Pro  Gln  Ile  Leu
               370                      375                      380

GAT  GAC  CCC  TGC  GCC  CAC  CTC  CTG  GGT  CCT  GAC  GGC  CTG  CCG  AAG  CCA       1201
Asp  Asp  Pro  Cys  Ala  His  Leu  Leu  Gly  Pro  Asp  Gly  Leu  Pro  Lys  Pro
          385                           390                      395

GCT  GCC  TGACTGCCTC  AGCAGGGACC  GCATGCCGCT  TGGAGAAGGG  GTGGCCTCGC              1257
Ala  Ala
400

CGGAGCTAGG  GAGCGGATGT  GGTGGGCTGG  CCGGACTCCT  GGGACATGTG  GGTGGTGGCT             1317

TGACCCCGGG  CCCATGGGCA  GCTTGCTGTG  GGGCAGTGCA  GGGAGTCCTG  CGGCCGCCCA             1377

GGTGTCAGGA  GAGGTCCCCG  CCGAGTGCTT  CAGCTGCCCT  AAGCTGCACC  AGCGCTTTGC             1437

CAAGATGGGA  TGGGGAGGGG  GTATGAGAAC  TGGCAGAGCC  TCGGTGCAGC  AGGGCTGAAG             1497

GGCTTTCTCA  CCCCAGCTCT  GGCTATGCCC  AGTTCTCTGA  GAAAGGAGCT  CAGTGGGGAG             1557

GTGGTCCCTC  CAGCGGACCA  GGGAAGGGGT  CACTGTGCTG  GGAGCAGCCT  CCTTGGGCCT             1617

CAGGAAACCA  CCAAGTGCCT  CGGATGGTGG  CTGCCCACGG  CGCTTCTGCT  GAGACCCTGC             1677

CCCCGGCCCA  GGTGTCTCGG  AGGGTGGCTG  CCCACGGCCT  GGGTGTGGCT  GGAATGGTGG             1737

CAGGAGTGGG  CACCAGTGCG  GCCCCGGTGG  CCATGGGGAA  TAAACCAGCA  TTGCTGCCAA             1797

AAA                                                                                1800
```

( 2 ) INFORMATION FOR SEQ ID NO:2:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Ser  Glu  Lys  Pro  Leu  Ala  Ala  Val  Thr  Cys  Thr  Ala  Pro  Val
1                   5                        10                       15

Asn  Ile  Ala  Val  Ile  Lys  Tyr  Trp  Gly  Lys  Arg  Asp  Glu  Glu  Leu  Val
               20                       25                       30

Leu  Pro  Ile  Asn  Ser  Ser  Leu  Ser  Val  Thr  Leu  His  Gln  Asp  Gln  Leu
```

|       |       |       |       |       | 35    |       |       |       |       | 40    |       |       |       |       | 45    |       |
|-------|-------|-------|-------|-------|-------|-------|-------|-------|-------|-------|-------|-------|-------|-------|-------|-------|

Lys Thr Thr Thr Thr Ala Val Ile Ser Lys Asp Phe Thr Glu Asp Arg
    50                      55                60

Ile Trp Leu Asn Gly Arg Glu Glu Asp Val Gly Gln Pro Arg Leu Gln
65                70                75                80

Ala Cys Leu Arg Glu Ile Arg Cys Leu Ala Arg Lys Arg Arg Asn Ser
              85              90              95

Arg Asp Gly Asp Pro Leu Pro Ser Ser Leu Ser Cys Lys Val His Val
        100            105            110

Ala Ser Val Asn Asn Phe Pro Thr Ala Ala Gly Leu Ala Ser Ser Ala
    115                120            125

Ala Gly Tyr Ala Cys Leu Ala Tyr Thr Leu Ala Arg Val Tyr Gly Val
    130                135            140

Glu Ser Asp Leu Ser Glu Val Ala Arg Arg Gly Ser Gly Ser Ala Cys
145                150            155            160

Arg Ser Leu Tyr Gly Gly Phe Val Glu Trp Gln Met Gly Glu Gln Ala
            165            170            175

Asp Gly Lys Asp Ser Ile Ala Arg Gln Val Ala Pro Glu Ser His Trp
        180            185            190

Pro Glu Leu Arg Val Leu Ile Leu Val Val Ser Ala Glu Lys Lys Leu
    195                200            205

Thr Gly Ser Thr Val Gly Met Arg Ala Ser Val Glu Thr Ser Pro Leu
    210                215            220

Leu Arg Phe Arg Ala Glu Ser Val Val Pro Ala Arg Met Ala Glu Met
225                230            235            240

Ala Arg Cys Ile Arg Glu Arg Asp Phe Pro Ser Phe Ala Gln Leu Thr
            245            250            255

Met Lys Asp Ser Asn Gln Phe His Ala Thr Cys Leu Asp Thr Phe Pro
        260            265            270

Pro Ile Ser Tyr Leu Asn Ala Ile Ser Trp Arg Ile Ile His Leu Val
        275            280            285

His Arg Phe Asn Ala His His Gly Asp Thr Lys Val Ala Tyr Thr Phe
    290                295            300

Asp Ala Gly Pro Asn Ala Val Ile Phe Thr Leu Asp Asp Thr Val Ala
305                310            315            320

Glu Phe Val Ala Ala Val Trp His Gly Phe Pro Pro Gly Ser Asn Gly
            325            330            335

Asp Thr Phe Leu Lys Gly Leu Gln Val Arg Pro Ala Pro Leu Ser Ala
            340            345            350

Glu Leu Gln Ala Ala Leu Ala Met Glu Pro Thr Pro Gly Gly Val Lys
    355                360            365

Tyr Ile Ile Val Thr Gln Val Gly Pro Gly Pro Gln Ile Leu Asp Asp
    370                375            380

Pro Cys Ala His Leu Leu Gly Pro Asp Gly Leu Pro Lys Pro Ala Ala
385                390            395            400

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:3:

| Val | Ala | Tyr | Thr | Phe | Asp | Ala | Gly | Pro | Asn | Ala | Val | Ile | Phe | Thr | Leu |
|---|---|---|---|---|---|---|---|---|---|---|---|---|---|---|---|
| 1 | | | | 5 | | | | | 10 | | | | | 15 | |

| Glu | Asp | Thr | Val | Ala | Glu | Phe | Val | Ala | Ala | Val | Arg |
|---|---|---|---|---|---|---|---|---|---|---|---|
| | | | 20 | | | | 25 | | | | |

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GGCCACATGC ACCTTATAGC         20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CTGTGAAGTC CTTGCTAATG G         21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

ACTCTGCACC AGGACCAGTT         20

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

GACCATGGCC TCGGAGAAG         19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

CAGCAATGCT GGTTTATTC                                                                                    19

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

ACGGGATCCA TATGGCCTCG GAG                                                                               23

DNA CODING SEQUENCES FOR MEVALONATE PYROPHOSPHATE DECARBOXYLASE

FIELD OF THE INVENTION

This application claims priority of Provisional Application 60/005,652 filed Oct. 18, 1995. The present invention relates to DNA sequences that code for Mevalonate Pyrophosphate Decarboxylase (MPD). This invention therefore allows the recombinant production of MPD, which in purity and in specific activity is superior to other sources of the protein.

BACKGROUND OF THE INVENTION

The enzyme mevalonate pyrophosphate decarboxylase (MPD) is one of the enzymes in the biosynthetic pathway of cholesterol from acetate. This enzyme converts the 6-carbon compound mevalonic pyrophosphate into isopentenyl pyrophosphate—the 5-carbon isoprene building block of a family of compounds. This portion of the cholesterol biosynthesis pathway is poorly understood (Prous, (1993) Drug News Perspectives 6 (6): 422–423), such that MPD serves as a new potential site to alter serum cholesterol levels.

MPD, which performs the first committed step in the biosynthesis of cholesterol, has been purified from several animal sources but no detailed examination of it or its mechanism has been provided. For example, the reaction is known to require the hydrolysis of ATP which is unusual for the decarboxylation of a β-hydroxy carboxylic acid. The ability to obtain large quantities of MPD would be useful in the development of potential drugs. To obtain such quantities, it is desirable to clone and to express it so that potential therapeutics could be developed to regulate and control cholesterol synthesis. This requires the obtention of an appropriate gene, which until now has not been achieved.

Interest in controlling human cholesterol metabolism makes MPD useful as a potential target for drug intervention. Inhibition of MPD could also have therapeutic applicability to treating cell proliferation (Cuthbert and Lipsky, (1995) Cancer Res. 55: 1732–1740), lymphomas (Cuthbert and Lipsky, (1990) J. Biol. Chem. 265: 18568–18575) and phenylketonuria (Castillo et al., (1991) Mol. Cell. Biol. 105: 21–25). Therefore, the present invention provides the genetic information necessary to recombinantly produce MPD in large quantities and to a high degree of purity.

SUMMARY OF THE INVENTION

The present invention relates to a nucleotide sequence that codes for human mevalonate pyrophosphate decarboxylase comprising a nucleotide sequence, which when expressed in a host cell results in the production of active mevalonate pyrophosphate decarboxylase.

The present invention also relates to an assay for measuring the ability of a compound to regulate the activity of mevalonate pyrophosphate decarboxylase comprising:

a) measuring the mevalonate pyrophosphate decarboxylase activity of a protein recombinantly produced by the expression of a nucleotide sequence according to claim 1 in the presence of a candidate compound;

b) comparing the mevalonate pyrophosphate decarboxylase activity in the presence of the candidate compound to mevalonate pyrophosphate decarboxylase activity of the protein.

DETAILED DESCRIPTION OF THE INVENTION

The present invention relates to a nucleotide sequence that codes for human mevalonate pyrophosphate decarboxylase comprising a nucleotide sequence, which when expressed in a host cell results in the production of active mevalonate pyrophosphate decarboxylase.

The nucleotide sequence of the present invention codes for active MPD when expressed in a host cell. The nucleotide sequence therefore can be any sequence similar to SEQ. ID. NO.: 1, so long as it codes for an amino acid sequence that is an active MPD. By similar to the sequence in SEQ. ID. NO.: 1, it is meant that variations in the nucleotide sequence can occur to use alternative codons to code for the same amino acid sequence as described in SEQ. ID. NO.: 2. This may be desirable so as to choose codons that are preferred to a particular host cell. Such codons are well described in the prior art. The nucleotide sequence can also be varied from the sequence in SEQ. ID. NO.: 1 so long as the variation does not result in the production of an inactive MPD as described in the present invention. The nucleotide sequence can also be considered to be similar if there are a minimal number of substitutions, additions or deletions so that the nucleotide sequence (or the protein for which it codes) is still considered a match. Various sequence programs describe what is considered a match, with a typical measurement being the smallest sum probability (N value) that two sequences are the same. For example, see Altschul et al., (1990) J. Mol. Biol. 215: 403–410, which describes the calculations for determining the smallest sum probability for the BLAST searches of database sequences. For pupose of this invention, a preferred sequence will be considered to be similar if its smallest sum probability is less than about $10^{-5}$, more preferably less than about $10^{-6}$, more preferably less than about $10^{-7}$. The same concept of similarity applies to peptide sequences. In fact, the peptide sequence is often the more important parameter with regard to enzyme activity. One can easily imagine a significant change in DNA sequence which would not significantly change the protein sequence.

MPD activity can be determined by measuring physical characteristics of the expressed MPD or its enzymatic activity. Physical characteristics that can be measured include one or more of the following: similar amino acid sequence, Michaelis-Menton constants (Km), weight of the holoenzyme, terminal nucleotide sequence corresponding to an appropriate terminal amino acid sequence, pI, and inhibition constants (Ki) of various inhibitors. Suitable mevalonate pyrophosphate Km's for MPD are from about 1 $\mu$M to about 50 $\mu$M, preferably from about 1 $\mu$M to about 10 $\mu$M. Suitable weights for the holoenzyme are from about 75 to about 150 kDa, preferably from about 85 kDa to about 100 kDa. Terminal amino acid sequence can be either the N- or C-terminal amino acid and can be any length, although a length of at least 10% of the full length sequence is preferred. More preferably, the length of a terminal amino acid sequence is at least about 50% of the full length sequence.

Enzymatic activity can typically be measured by the coupled spectrophotometric assay of Cardemil and Jabalquinto or as the conversion of labelled mevalonate pyrophosphate into isopentenyl pyrophosphate (IPP) (Cardemil and Jabalquinto, (1985) Methods Enzymol. 110: 86–92). The latter method is more preferred for the measurement of MPD activity in crude cell extracts.

The preferred sequence of the nucleotides of the present invention, will have a sequence similar to the sequence according to FIG. 1 and it allow the production of MPD activity. Preferably, the additional MPD activity will be enzymatic activity.

The nucleotide sequence of the present invention is expressed in a suitable host cell to produce active MPD protein. Expression occurs by placing a nucleotide sequence of the invention into an appropriate expression vector and introducing the expression vector into a suitable host cell, growing the transformed host cell, inducing the expression of MPD, and purifying the recombinant MPD from the host cell to obtain purified and active MPD. Appropriate expression vectors are known in the art. For example, pET-14b, pCDNA1Amp, and pVL1392 are available from Novagen and Invitrogen and are suitable vectors for expression in *E. coli*, COS cells and baculovirus infected insect cells, respectively. These vectors are illustrative of those that are known in the art. Suitable host cells can be any cell capable of growth in a suitable media and allowing purification of the expressed MPD. Examples of suitable host cells include *E. coli* (e.g., strain DHIQ Gibco-BRL (Gaithersburg, Md.), or strain BL21(DE3), Novagen, (Madison, Wis.), baculovirus infected cell cultures (such as insect cell cultures including SF9 cells), yeast (such as Pichea) and mammalian cells (such as COS monkey cells as described in for example Sambrook et al., *Molecular Cloning, A Laboratory Manual*, 2nd Edition (1989), Cold Spring Harbor Press, Cold Spring Harbor, N.Y. Expression in *E. coli* often results in expression of the MPD in inclusion bodies which may require a modification in the purification procedure. Another possible alternative is to express the MPD at the organism level, for example in plants or higher animals. Baculovirus infection of insect larvae and harvesting of the insect larvae for expressed proteins ("catapillar harvest") has also been achieved for various proteins to produce active protein (e.g., Luckow, (1993) Curr. Opin. Biotechnol. 4: 564–572; Pajot-Augy et al., (1995) J. Mol. Endocrinol. 14: 51– 66). The preferred expression system for the present invention is baculovirus infected insect cell cultures.

Growth of the transformed host cells can occur under conditions that are known in the art. The conditions will generally depend upon the host cell and the type of vector used. Suitable induction conditions may be used such as temperature and chemicals and will depend on the type of promoter utilized. When baculovirus infected insect cells are used, preferred conditions for fermentation include using Grace's insect media (Luckow and Summers (1988) Virology 170: 31–39) at about room temperature.

Purification of the MPD can be accomplished using known techniques without performing undue experimentation. Generally, the transformed cells expressing the MPD are broken, crude purification occurs to remove debris and some contaminating proteins, followed by chromatography to further purify the MPD to the desired level of purity. Cells can be broken by known techniques such as homongenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatogaphy (HPLC), gel filtration, affinity chromatography, hydrophobic interaction chromatography, etc. Because active MPD usually exists as a dimer, dithiothreitol (DTT) may be used during all or some of the purification to prevent improper folding of the MPD and loss of activity. It is particularly advisable to use DTT as purity to prevent inactivation. A preferred purification method for baculovirus infected insect cells can include sonication, ammonium sulfate precipitation (40–70% cut), hydrophobic interaction column (preferably phenyl sepharose), followed by anion exchange chromatography (preferably mono-Q sepharose). DTT is preferably used during the anion exchange chromatography.

Therefore, the nucleotide sequences of the present invention result in the production of active mevalonate pyrophosphate decarboxylase (MPD) when expressed in a suitable host cell and purified.

The nucleotide sequences of the present invention are useful for producing large quantities of MPD, preferably human MPD, to be used in assays to screen for inhibitors of MPD. Potential therapeutics can be developed to regulate and control cholesterol synthesis and cell proliferation. Such assays typically include measuring the enzymatic activity of MPD both as a control and in the presence of a potential inhibitor.

Therefore, an assay for measuring the ability of a compound to regulate the activity of mevalonate pyrophosphate decarboxylase comprises:

a) measuring the mevalonate pyrophosphate decarboxylase activity of a protein recombinantly produced by the expression of a nucleotide sequence coding for MPD in the presence of a candidate compound; and b) comparing the mevalonate pyrophosphate decarboxylase activity in the presence of the candidate compound to mevalonate pyrophosphate decarboxylase activity of the protein. The comparison can be a direct comparison to a control enzyme assay in the absence of the candidate compound or it can be a comparison to a reference value for MPD activity obtained previously. In other words, the assays of the present invention do not require a direct comparison to a control assay for every candidate although such a direct comparison is preferred and recommended.

Interest in controlling human cholesterol metabolism makes large amounts of MPD useful as a potential target for drug intervention. Inhibition of MPD by inhibitors could also have therapeutic applicability in treating cell proliferation, lymphomas and phenylketonuria. MPD, when produced in large amounts could also be useful as molecular weight markers, or as dietary food supplement of proteins. Therefore, the present invention provides the genetic information necessary to recombinantly produce MPD in large quantities.

The nucleotide sequences of the present invention are also useful for producing large quantities of MPD, preferably human MPD, to be used as a starting material in the chemical synthesis of polyisoprene-containing compounds that include, but are not limited to, taxol.

The nucleotide sequence for MPD can also be used to produce MPD protein and to use that MPD protein to generate antisera to be used as an aid in the diagnosis of patients suffering from metabolic diseases that affect the cholesterol synthetic pathway. Examples of such diseases include, but are not limited to, Zellweger syndrome, characterized by a loss of peroxisomes, and mevalonate kinase deficiency.

All references cited in this specification are hereby incorporated by reference.

EXAMPLES

The examples are provided to describe specific emobodiments of the invention and are not to be construed as limiting the the invention in any way.

Example 1

General Materials and Methods

The human liver MPD cDNA sequence was isolated using DNA sequence information obtained originally from a partial cDNA of rat liver MPD. Briefly, rat liver MPD was purified, subjected to trypsin digestion, then the resulting peptides isolated and sequenced. From one of the peptides PCR primers were designed to amplify the corresponding cDNA fragment from a rat liver cDNA.

Standard cloning and expression techniques were used. Transient expression in COS cells was performed as in Sambrook et al., *Molecular Cloning, A Laboratory Manual*, 2nd Edition (1989), Cold Spring Harbor Press, Cold Spring Harbor, N.Y. Baculovirus expression in SF9 cells was performed as described in Luckow, (1993) Curr. Opin. Biotechnol. 4: 564–572; Pajot-Augy et al., (1995) J. Mol. Endocrinol. 14: 51–66. Unless specifically mentioned, all enzymes were obtained from Boehinger-Mannheim or New England Biolabs, all chemical were from Sigma Chemical Co., and all kits were used according to the manufacturer's specifications. Plasmids pCRII, pVL1392, pcDNAIAmp, and the PCR optimizer kit were from Invitrogen. Plasmid pET-14b and *E. coli* strain BL21(DE3) were obtained from Novagen. cDNA libraries were from Stratagene. Kits for 5' RACE, 3' RACE, and total RNA isolation were obtained from GIBCO-BRL. PCR reactions were performed using the GeneAmp kit from Perkin-Elmer Cetus. Protein concentrations were determined with the Bio-Rad protein assay (BIO-RAD). Oligonucleotides were made by Biosynthesis. The GeneWorks (IntelliGenetics, Inc.) sequence analysis system version 2.3 was used with the default parameters.

Example 2

Purification of Rat Liver Mevalonate Pyrophosphate Decarboxylase (MPD)

Purification of rat MPD was accomplished using six steps, four of which are chromatography columns. The purification protocol was performed at 4° C. unless indicated otherwise. All buffers were pH adjusted at room temperature (rt). Livers from 6 freshly sacrificed rats (84 g) were collected on ice, rinsed in homogenization buffer (20 mM Tris/HCl pH 7.5, 250 mM sucrose, 15 mM EDTA, 15 mM EGTA), diced and homogenized with 300 ml of the same solution containing 0.1 mM leupeptin, 0.75 mg/l Aprotinin, and 0.1 mM phenylmethanesulfonyl fluoride. After centrifugation at 4° C. for 40 min at 38,000× g, a 45% to 55% ammonium sulfate fractionation of the supernatant was made.

The ammonium sulfate pellet from the 45%–55% saturation fraction was resuspended in buffer A (50 mM Tris/HCl pH 7.5, 2.3 mM $MgCl_2$, 0.2 mM ATP, 0.2 mM DTT) and applied to a PD-10 (Pharmacia) gel filtration column to remove the ammonium sufate. The sample was then applied to a 10 ml EAH Sepharose 4B (Pharmacia) column to which p-coumaric acid was coupled using the procedure of Bhat and Ramasarma, (1980) Indian J. Biochem. Biophys. 17: 249–254. The column was washed with 50 ml of buffer A and with 30 ml of 50% buffer A/50% buffer A with potassium phosphate pH 6.9 substituted for the Tris/HCl. Activity was eluted with 35 ml of buffer A containing potassium phosphate.

The active fraction from the p-coumaric acid column was brought to 1.3M with solid ammonium sulfate and applied to a 10 ml Phenyl-Sepharose (Pharmacia) column in 50 mM potassium phosphate pH 6.9. A 1.3M to 0M linear gradient in 100 ml was performed at rt, and the active fractions were pooled, concentrated by membrane filtration using a Centricon-30 (Amersham), and washed with buffer A to remove ammonium sulfate.

The active fractions from the Phenyl-Sepharose column were loaded onto a rt Mono P column (Pharmacia) preequilibrated in 25 mM BisTris/HCl pH 6.3, 2 mM MgCl2, 1 mM ATP. 10% Polybuffer 64 (Pharmacia) with 2 mM $MgCl_2$, 1 mM ATP, pH 4.0 was used to elute the active material which was found to be at pH 5.8.

Active fractions from the Mono P column were pooled, concentrated with a Centricon-30, and applied to a rt Mono Q column (Pharmacia) in 20 mM Tris/HCL pH 8.0. A linear gradient of 0M to 0.8M NaCl was performed and the active fractions were pooled and concentrated. Glycerol was added to 50% for −20° C. storage.

A Showdex KW-803 gel filtration column was used to determine the size of the holoenzyme at rt. The buffer contained 150 mM NaCl, 50 mM Tris/ HCl pH 8.0, 2 mM $MgCl_2$, 1 mM ATP. Suitable protein standards placed the size of rat liver MPD around 100 kDa; between the 158 kDa and 48 kDa gel filtration protein standards (BioRad). A 10% discontinuous SDS polyacrylamide gel (Laemmli, (1970) Nature 227: 680–685) was used to visualize the purified rat liver MPD.

The rat liver MPD was purified nearly 5,000-fold to over 90% purity as judged by SDS-PAGE. This was achieved using 6 steps with four column chromatography runs. Gel filtration analysis indicated that the rat liver MPD enzyme is a homodimer on 45 kDa subunits. The rat liver MPD purified by this method was similar to chicken liver (Alvear et al., Biochemistry (1982) 21: 4646–4650) and pig liver (Chiew et al., (1987) Biochem. Biophys. Acta 916, 271–278) enzymes in regard to specific activity, Km for MevPP, and holoenzyme composition.

Example 3

Designing PCR Primers From Purified MPD and Obtaining MPD cDNA from Rat Library and a Purported Human Library The purified rat MPD from Example 2 was subjected to standard trypsin digestion. The resulting peptides were isolated and sequenced. One of the peptides NT71 (Val-Ala-Tyr-Thr-Phe-Asp-Ala-Gly-Pro-Asn-Ala-Val-Ile-Phe-Thr-Leu-Glu-Asp-Thr-Val-Ala-Glu-Phe-Val-Ala-Ala-Val-Arg) (SEQ. ID.No.: 3), was used to design primers to amplify the corresponding cDNA from a rat liver cDNA library (Stratagene #936513). This PCR reaction produced a DNA fragment which matched the amino acid sequence of the peptide. An oligonucleotide that corresponded to the unique DNA sequence between the PCR primers was then used to probe $10^6$ pfu of the same rat liver cDNA library. Three identical clones were isolated and sequenced from this library, however analysis suggested that only the last half of the open reading frame (ORF) was encoded.

This partial cDNA clone was then used to probe what was advertised as a human liver cDNA library (Stratagene #937220). 11 positive clones were isolated and sequenced, the largest of which encoded only 90% of the ORF. Subsequent to demonstration of activity with human liver cDNA (see below), we were informed by Stratagene that the advertised human liver cDNA library was actually made from a non-human tissue. Because we used human liver RNA to directly isolate the cDNA sequence shown in SEQ. ID. NO.: 1, this accident did not alter our final results.

Example 4

Obtaining 5' and 3' End of MPD cDNA Using RACE Experiments and Generation of Full Length MPD We performed 5' RACE experiments to determine the 5' end of the mRNA for human liver MPD. We used two independent sources of human liver RNA and obtained identical results with both preparations. We designed the primers for the 5' RACE experiments with DNA sequence of the clone that encoded only 90% of an ORF (see above). At that time we did not know that the 90% clone came from a nonhuman tissue. In spite of the sequence differences due to the nonhuman source of the primer sequence, we nevertheless obtained the 5' end of the human liver MPD cDNA (nucleotides 1 to 170 of SEQ. ID. NO.: 1).

The RACE experiments and subcloning were performed as follows. Total RNA was isolated from a frozen specimen of human liver. Purified human liver mRNA was purchased from Clontech. Primers used for the 5' RACE experiments were: GSP1 (gene specific primer 1), GGCCACATGCAC-CTTATAGC (SEQ. ID No.: 4); and GSP2, CTGTGAAGTC-CTTGCTAATGG (SEQ. ID No.: 5). PCR conditions were 40 cycles of 94° C.-1 min., 50° C.-1 min, 72° C.-2 min and produced a 230 bp band which was subcloned into pCRII and sequenced.

Using the DNA sequence from the 5' RACE, we performed a 3' RACE experiment which revealed the 3' end of the human liver MPD cDNA (nucleotides 151 to 1812 of SEQ. ID. NO.: 1).

The primers used for the 3' RACE experiment were ACTCTGCACCAGGACCAGTT (GSP3)(SEQ. ID No.: 6) and the UAP primer from the 3' RACE kit. To obtain the correct band, PCR conditions were altered using the PCR Optimizer kit. Final conditions were: 30 mM Tris-HCl pH 9.0,7.5 mM $(NH_4)SO_4$, 1.3 mM $MgCl_2$, 10% DMSO; 30 cycles of 94° C.-1 min, 42° C.-1 min, 72° C.-2 min.

The information obtained from the 5' and 3' RACE experiments allowed us to design primers for a PCR reaction that would produce a full-length cDNA of the enzyme. The primers for the full-length amplification of MPD cDNA were: 5' primer-GACCATGGCCTCGGAGAAG (SEQ. ID No.: 7) and 3' primer-CAGCAATGCTGGTTTATTC (SEQ. ID No.: 8). Conditions for the amplification were the same as for the 3' RACE. DNA bands were cloned into pCRII and sequenced as above. FIG. 1 shows the consensus cDNA sequence we obtained from this full-length PCR reaction. We sequenced 3 clones from two independent PCR reactions and found base-substitution discrepancies among the 3 clones at a frequency of 0.003 per base pair. In all cases of a discrepancy, two out of three clones were identical. The nucleotide from the two identical clones was presumed to be the correct base and this is shown in SEQ. ID. NO.: 1.

Example 5

Expression of MPD cDNA

The 1.8 kbp fragment of DNA amplified from the full-length PCR reaction was modified by another PCR reaction to generate restriction sites for subcloning. The PCR primers used to modify the cDNA for subcloning were: 5'Nde-ACGGGATCCATATGGCCTCGGAG (SEQ. ID No.: 9) and the 3' primer of the full length amplification shown in Example 4. Standard PCR conditions of 40 cycles at 94° C. (1 min), 50° C. (1 min), 72° C. (2 min), using the 1.8 kbp full-length DNA fragment were performed. This generated the restriction sites for NdeI and XhoI. The resulting amplified product was cloned into pCRII to give p11. From p11, we subcloned the modified full-length cDNA into pET-14b using NdeI and XhoI (p11-4), and into pcDNAIAmp (p11-1) and pVL1392 (PVL5) using EcoR1.

The resulting fragment was inserted into the PCR-subcloning vector pCRII and sequenced. The same cDNA fragment was subcloned into the E. coli T7 expression vector pET-14b, the eukaryotic expression vector pCDNAIAmp, and the baculovirus expression vector pVL1392. Shown in Table 1 are the enzyme activity levels of extracts made from cells with these expression systems. In all systems the cells containing the cDNA insert for human liver MPD showed significantly higher levels of activity compared to the control cells. Because E. coli does not possess MPD activity its presence in any extract proves that we have cloned and expressed the human enzyme.

All expression experiments were carried out using a cDNA which was later found to have 5 mutations compared to the consensus sequence of SEQ. ID. NO.: 1. Three of these mutations were coding changes (a44t to give Thr13Ser; g514c to give Glu169Asp; and t1163a to give Cys386Ser). The other two mutations were noncoding mutations (t661g to give AGT to AGG at Ser218, and a1560g which is in the 3' noncoding region). When the coding changes were mutated back to the consensus sequence in plasmid pO-32 (a derivative of PETq4-b) and expressed in the E. coli system, no significant difference in activity was observed as shown in Table 1.

Example 6

In Vitro Mutagenesis

Plasmid p11 has an f1 origin of replication and was used to produce single-stranded DNA as the template for site-directed mutagenesis. The Sculptor Amersham) in vitro mutagenesis kit was used to convert p11 (with the three coding mutations compared to SEQ. ID. NO.: 1) to pO-3 using three mutagenic oligonucleotides at one time. Plasmid pO-3 was subcloned into pET14-b to give pO-32 which was subsequently transformed into BL21(DE3) for expression as described in Example 5 above.

The reason the Arg residues were mutated is because we found that partially purified human liver MPD was inhibited by phenylgloxal. This agrees with the work of Jabalquinto et al., (1983) Arch. Biochem. Biophys. 225: 338, who showed that chicken liver MPD was inactivated by the arginine-modifying compound phenylgloxal with a pseudo-first order kinetics. They also found that ATP and MevPP could protect against this inactivation. They concluded that a single arginine is near the binding site of ATP and MevPP in the chicken liver enzyme. To this end, the Arg27Lys and Arg153Lys mutants were made using the AAA lysine codon triplet and a single-stranded DNA template isolated from pO-3. These mutated cDNAs were subcloned into pET14-b and expressed like p11-4 as described above. As shown in Table 1, the Arg153Lys mutant is devoid of MPD activity indicating that this amino acid is probably near the active site and is likely to be the site of phenylglyoxal inactivation. The Arg27Lys mutant appears to produce lower activity compared to the parent plasmid (pO-32) from which it was derived, but this may not be a significant difference. Western blots of the extracts revealed that similar levels of immune-reactive material were produced in all of the E. coli extracts, indicating that differences in protein expression were not a problem. Antisera against MPD for the Westerns was made with material expressed in E. coli from plasmid p11-4.

Example 7

Purification of Recombinant MPD

The purification of recombinant MPD was accomplished using known techniques. Generally, a cell extract was obtained, followed by NH$_4$SO$_4$ precipitation, hydrophobic interaction chromatography and ion exchange chromatography. The infected cells were centrifuged and the pellet resuspended in 10 ml of homogenization buffer (20 mM Tris/HCl pH 7.5 at 20° C., 15 mM EGTA, 100 μM Leupeptin, 0.75 mg/1 Aprotinin, 0.1 mM phenylmethanesulfonyl flouride). The resuspended solution was sonicated three times at setting 3 for 10 seconds each. The sonicated cell extract was usually assayed directly for activity. It was also further purified on occasion as follows.

The sonicated cell extract was centrifuged in a Sorvall SS34 rotor at 4° C., 10,000 RPM for 10 minutes. To 10 ml of the supernatant from the extract, NH$_4$SO$_4$ was added and the 40–70% fraction collected. To the resuspended 40–70% fraction, NH$_4$SO$_4$ was added to a concentration of 1.3M and applied to a 10 ml phenyl sepharose column (Pharmacia) (hydrophobic interaction chromatography) preequilibrated with 50 mM KPi, pH 7.5–7.6. Elution occurred with a gradient of NH$_4$SO$_4$ from 1.3M to 0M with a flow rate of 100 ml/4 hr. The results through the hydrophobic interaction chromatography step produced a yield of about 50% for MPD that was about 50% pure. The four fractions (out of a total of 34 fractions) with the highest specific activity were pooled and concentrated using a Centricon-30 (Amicon). The pooled fractions were then loaded onto an anion exchange chromatography column (mono-Q, Pharmacia), 20 mM Tris/HCl pH 8.0, 1 mM dithiothreitol (DTT) and a flow rate of 1 ml/min). Elution was performed using a salt gradient from 0–0.6M NaCl over 30 min.

The use of the DTT was important to maintain activity during elution. This was determined using gel filtration wherein the concentrate from the pooled fractions was loaded unto a Superdex 200 HR 10/30 column with working buffer (50 mM BisTris/HCl, pH 7.0, 0.1M NaCl and 1 mM dithiothreitol (DTT)). Elution occured with a salt wash of 20 mM BisTris/HCl, pH 7.5–7.6, 150 mM NaCl both with and without 1 mM DTT. Those elutions without DTT showed significantly less activity than the elutions with DTT and a shift of the molecular weight towards the monomer. It is likely that the DTT maintains the MPD in the dimer configuration, which is the native state for active MPD.

The overall result of the purification scheme was a purity of at least 90% as measured by gel electrphoreisis.

Example 8

Enzyme Assays

Cell pellets from the various expression systems were sonicated in homogenization buffer (20 mM Tris/HCl pH 7.5, 15 mM EDTA, 15 mM EGTA, 100 μM Leupeptin, 0.75 mg/l Aprotinin, 0.1 mM PMSF) and assayed directly for enzyme activity and protein concentration. Activity was measured as the conversion of labelled mevalonate pyrophosphate into isopentenyl pyrophosphate. The assay solution contained 50 mM BisTris/HCl pH 7.0 at 20° C., 1 mM DTT, 3.8 mM MgSO$_4$, 5.8 mM ATP and 1.9 μM 3-$^{14}$C-mevalonate pyrophosphate (New England Nuclear—54 mCi/mmole). Assays were conducted at 37° C. for 1 hr. To stop the reaction and to convert the substrates/products, 2 mg of alkaline phosphatase (Sigma P-3877) dissolved in 25 μl of 1M Tris was then added and the mixture was incubated for 30 min more. 2 ml of Econofluor-2 (New England Nuclear) was added to the assay mixture the sample was capped, shaken, and counted on a scintillation counter. Because of the organic nature of the scintillation fluid, dephosphorylated product (isopentenyl) is solubilized and counted whereas dephosphorylated substrate (mevalonic acid) is not. A "no enzyme" sample is used to correct for background.

Example 9

Comparison of MPD Sequences

We searched the cDNA and the deduced protein sequence of human liver MPD for similarity against the Genbank 83, UEMBL39, and SWISS-PROT 28 data banks using the GeneWorks similarity search programs. In our estimation the only significant resemblence was found with the deduced protein sequence from an unidentified and incomplete ORF adjacent to the COQ2 gene of Saccharomyces cerevisiae. We suggest that the unidentified ORF is the yeast MPD gene. Because COQ2 encodes the structural gene for para-Hydroxybenzoate:polyprenyltransferase it appears that this region of the yeast genome is rich in genes related to isoprene metabolism.

DNA sequence identity to MPD was found to several expression sequence tag clones: Genbank Numbers: T09120, T09119, T15476, T96443, T09350, T09432 and HSC1OB102. The T09120 clone was derived from a human infant brain cDNA library (clone HIBBP29) and was also reported to have similarity to the ORF adjacent to the COQ2 gene of yeast. The EST clone was obtained (ATCC#85596) and sequenced. The sequence was identical to SEQ. ID. NO.: 1 except for a base deletion midway through the ORF which prematurely terminates the protein. Assuming that this base deletion was an error in library construction, we believe that the MPD in the fetal human brain should be identical to that in the human liver.

TABLE 1

Activity of expression systems with human MPD cDNA inserts

| System | Strain | Activity |
| --- | --- | --- |
| E. coli | no plasmid | <10 |
|  | p11-4 | 7000 |
|  | pO-32 | 8600 |
|  | pArg27Lys | 2600 |
|  | pArg153Lys | <10 |
| COS cells | no plasmid | 700 |
|  | p11-1 | 2900 |
| Baculovirus | no virus | 7500 |
| (SF9 cells) | clone #2 | 110000 |

What is claimed is:

1. An isolated DNA segment encoding a human mevalonate pyrophosphate decarbloxylase comprising a nucleotide sequence which, when expressed in a host cell, results in the production of an enzyme having human mevalonate pyrophosphate decarboxylase activity.

2. An isolated DNA segment according to claim 1 having a nucleotide sequence that codes for a protein that has an amino acid as represented by SEQ. ID. No.: 2.

3. An isolated DNA segment according to claim 1 having a nucleotide sequence as represented by SEQ. ID. No.: 1.

4. A nucleotide sequence comprising an isolated DNA segment that:
   a) codes for a mevalonate pyrophosphate decarboxylase protein, which when expressed in a host cell has enzymatic activity as measured by the coupled spectrophotometric assay, and
   b) has a nucleotide sequence coding for an amino acid sequence as represented by SEQ. ID. No.: 2.

5. A nucleotide sequence comprising an isolated DNA segment that:
   a) codes for a mevalonate pyrophosphate decarboxylase protein, which when expressed in a host cell has enzymatic activity as measured by the coupled spectrophotometric assay, and
   b) has a nucleotide sequence as represented by SEQ. ID. No.: 1.

6. A nucleotide sequence comprising an isolated DNA segment that:
   a) codes for a mevalonate pyrophosphate decarboxylase protein, which when expressed in a host cell has enzymatic activity as measured by the coupled spectrophotometric assay, and
   b) has a mutant nucleotide sequence as represented by SEQ. ID. No.: 1 wherein said mutant is selected from the group consisting of a44t, g514c, t1163a, t661g and a1560g.

7. A nucleotide sequence comprising an isolated DNA segment that:
   a) codes for a mevalonate pyrophosphate decarboxylase protein, which when expressed in a host cell has enzymatic activity as measured by the conversion of labelled mevalonate pyrophosphate into isopentenyl pyrophosphate, and
   b) has a nucleotide sequence coding for an amino acid sequence as represented by SEQ. ID. No.: 2.

8. A nucleotide sequence comprising an isolated DNA segment that:
   a) codes for a mevalonate pyrophosphate decarboxylase protein, which when expressed in a host cell has enzymatic activity as measured by the conversion of labelled mevalonate pyrophosphate into isopentenyl pyrophosphate, and
   b) has a nucleotide sequence as represented by SEQ. ID. No.: 1.

9. An isolated DNA segment according to claim 1 wherein said mevalonate pyrophosphate decarboxylase activity is measured by the coupled spectrophotometric assay or as the conversion of labeled mevalonate pyrophosphate into isopentenyl pyrophosphate.

10. An isolated DNA segment according to claim 9 wherein said mevalonate pyrophosphate decarboxylase activity is measured either as a Michaelis-Menton constant (Km) or by an inhibition constant (Ki) of an inhibitor.

11. An isolated DNA segment according to claim 1 wherein said mevalonate pyrophosphate decarboxylase is the holoenzyme having a weight of about 75 kDa to about 150 kDa.

12. An isolated DNA segment selected from the group consisting of a nucleotide sequence encoding amino acids from 1 through about 15 of SEQ. ID. No.: 2 and a nucleotide sequence encoding amino acids from about 385 through 400 of SEQ. ID. No.: 2.

* * * * *